United States Patent
De La Poterie et al.

(10) Patent No.: US 11,819,558 B2
(45) Date of Patent: Nov. 21, 2023

(54) METHOD FOR APPLYING FALSE EYELASHES AND MAKEUP METHOD

(71) Applicant: LVMH RECHERCHE, Saint Jean de Braye (FR)

(72) Inventors: Valérie De La Poterie, Lailly en Val (FR); Audrey Destrem, Saint Ay (FR); Laurent Nogueira, Paris (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 81 days.

(21) Appl. No.: 17/251,108

(22) PCT Filed: Jul. 12, 2019

(86) PCT No.: PCT/FR2019/051748
§ 371 (c)(1),
(2) Date: Dec. 10, 2020

(87) PCT Pub. No.: WO2020/012133
PCT Pub. Date: Jan. 16, 2020

(65) Prior Publication Data
US 2021/0177714 A1    Jun. 17, 2021

(30) Foreign Application Priority Data
Jul. 12, 2018 (FR) ...................... 1856438

(51) Int. Cl.
*A61K 8/25* (2006.01)
*A61Q 1/10* (2006.01)

(52) U.S. Cl.
CPC .................. *A61K 8/25* (2013.01); *A61Q 1/10* (2013.01); *A61K 2800/31* (2013.01); *A61K 2800/412* (2013.01); *A61K 2800/43* (2013.01); *A61K 2800/47* (2013.01); *A61K 2800/651* (2013.01)

(58) Field of Classification Search
CPC .................. A61Q 1/10; A61K 2800/31; A61K 2800/412; A61K 2800/43; A61K 2800/47; A61K 2800/651; A61K 8/25; A61K 8/19; A61K 8/04
See application file for complete search history.

(56) References Cited

U.S. PATENT DOCUMENTS 3,516,422 A * 6/1970 Bechtold .................. A41G 5/02
132/53
2007/0009454 A1   1/2007 Thevenet

FOREIGN PATENT DOCUMENTS

| EP | 1741363 | | 1/2007 |
| JP | H1160439 A | * | 3/1999 |
| JP | 3214988 U | | 2/2018 |
| WO | WO-2006037905 A1 | * | 4/2006 ............. A45D 33/00 |

OTHER PUBLICATIONS

Erdogan, S., Garboczi, E. and Fowler, D. (2007), Shape and Size of Microfine Aggregates: X-Ray Microcomputed Tomography vs. Laser Diffraction, Advanced Powder Technology, [online], https://tsapps.nist.gov/publication/get_pdf.cfm?pub_id=860681 (Accessed Jul. 13, 2022) (Year: 2007).*
Górka-Kostrubiec B, Szczepaniak-Wnuk I. Magnetic study of a mixture of magnetite and metallic iron in indoor dust samples. Air Qual Atmos Health. 2017;10(1):105-116. doi: 10.1007/s11869-016-0412-5. Epub Jun. 9, 2016. PMID: 28111597; PMCID: PMC5216106. (Year: 2017).*
PE2E translation of WO 2006037905 A1 (Year: 2006).*
International Search Report and Written Opinion issued for International Patent Application No. PCT/FR2019/051748, dated Oct. 28, 2019, 10 pages including English translation of Search Report.
Search Report issued for French Patent Application No. 1856438, dated Mar. 26, 2019, 2 pages.

* cited by examiner

*Primary Examiner* — Isaac Shomer
*Assistant Examiner* — Amanda Michelle Petritsch
(74) *Attorney, Agent, or Firm* — MH2 TECHNOLOGY LAW GROUP, LLP

(57) ABSTRACT

The present invention relates to a method for applying false eyelashes, comprising:
  a step of applying, on the root of the eyelashes of the eyelid of a person, a magnetic composition comprising fine magnetic particles; and
  a step of applying, on the composition deposited in the previous step, a magnetic false eyelash.

18 Claims, No Drawings

METHOD FOR APPLYING FALSE EYELASHES AND MAKEUP METHOD

CROSS-REFERENCE TO RELATED APPLICATIONS

This application is a U.S. National Stage application of International Application No. PCT/FR2019/051748 filed 12 Jul. 2019, which claims priority to French Application No. FR 1856438, filed 12 Jul. 2018, the entire disclosures of which are hereby incorporated by reference in their entireties.

The present invention relates to a method for applying false eyelashes in which a magnetic composition which can be applied as an eyeliner or an eyeshadow is used. The magnetic composition contains magnetic particles to serve as a means for fixing magnetic false eyelashes. The invention also relates to an eye makeup product comprising a magnetic composition and magnetic false eyelashes, the magnetic composition being a makeup composition.

PRIOR ART

Consumers who find the application of a mascara tricky to achieve, and those who seek an increase in volume and an elongation of eyelashes much greater than those that can be achieved with a mascara, resort to the application installation of fake eyelashes consisting of artificial eyelashes mounted on a base that is applied to the eyelid at the edges of the eyelashes.

False eyelashes usually used to improve the appearance of the fringe of natural eyelashes, in particular the volume, the length or the density, also make it possible to obtain different color effects.

Two methods of applying false eyelashes are known. Two methods for applying false eyelashes are known.

One method is to apply an adhesive glue on the eyelid and/or on the base of the false eyelash. However, many consumers prefer to avoid using glues known for the risks of allergy they cause.

Other disadvantages are associated with the use of a glue. For example, false eyelashes cannot be reused because, once taken off, accumulations of glue remain on their base. In addition, applying glue is still a delicate step that often requires the intervention of a professional. If the false eyelash was incorrectly fitted on the eyelid, it is difficult to reposition. It is also hard to find the right balance between the retention on the eyelid over time and the ease of removal when removing makeup. Increasing the fixing time of the false eyelashes is obtained to the detriment of the ease of detachment of the false eyelashes and of the removal of makeup glue remaining on the eyelid after the detachment of the false eyelashes. Some glues are therefore poorly tolerated since they are difficult to remove and cause pain when detaching the false eyelashes.

A second method for attaching false eyelashes uses the magnetic attraction force of two magnetic false eyelashes. The two false eyelashes, with opposite polarities, are applied on either side of the fringe of natural eyelashes, and remain in contact as long as the user does not separate them manually. This application method nevertheless has disadvantages. The presence of two false eyelashes on the same fringe of eyelashes weighs down the eyelid. This adversely affects the comfort of the user, and the makeup result is not always aesthetic. Moreover, the adjustment of the two false eyelashes depends on the relative position of the magnets on the base of each false eyelash: if two magnets with opposite polarity are not perfectly aligned at the time of application, the result is not optimal.

Therefore, the need remains for having a method for applying false eyelashes and eye makeup that is easier and faster to achieve, easier and faster to remove, which is aesthetically pleasing, and which allows the false eyelashes to be re-used several times. It is desirable for the makeup result to be natural and for the false eyelashes to conform to the shape of the eyelids.

GENERAL DESCRIPTION OF THE INVENTION

The present invention specifically addresses these needs and relates to a method for applying false eyelashes on a person, comprising:
  a step of applying, on the eyelid of the person, a magnetic composition comprising a homogeneous dispersion of magnetic particles; and
  a step of applying, on the magnetic composition deposited in the previous step, a false eyelash comprising a magnetic base and an eyelash fringe.

The magnetic composition can be an eyeliner or an eyeshadow. It can be applied on at least the part of the eyelid near the root of the eyelashes, and form a non-sticky film, onto which the magnetic base of the false eyelash is applied.

The invention also relates to an eyelash makeup product comprising at least one composition comprising magnetic particles, and at least one pair of false eyelashes with a magnetic base.

Finally, the invention relates to a magnetic makeup composition containing from 20% to 99% by mass of magnetic particles, the size of which particles is less than 150 microns.

The method of the invention preferably uses a composition that contains fine magnetic particles homogeneously distributed in a matrix in order to fix a magnetic false eyelash on the eyelid at the edges of the eyelashes. This matrix can be, for example, a polymer matrix, a matrix of powders or a matrix made up of wax(es) and oil(s). The method of the invention avoids both the use of a glue and the application of two false-eyelash fringes on either side of the natural eyelash fringe of the user.

The method of the invention allows easy detachment of the false eyelash from the eyelid, and rapid removal of the composition, using a conventional makeup remover. The false eyelash can remain in place for a whole day and can be easily repositioned or put back in place should it fall.

The method of the invention also allows the user to easily remove and reapply the false eyelash as long as the magnetic composition remains in place on the eyelid.

The composition, which can be an eyeliner or an eyeshadow, is not sticky. The composition film that is left on the eyelid is homogeneous and thin.

Finally, the method of the invention allows very easy access to a wide range of makeup effects ranging from very natural to very sophisticated, without having to use a professional. The false eyelashes can be customized according to the shape of the eyelid of the user and can be reused as many times as the user desires.

DETAILED DESCRIPTION OF THE INVENTION

The invention relates to a method for applying false eyelashes on a person, comprising:
  a step of applying, on the eyelid, a magnetic composition comprising a homogeneous dispersion of magnetic particles, said magnetic particles comprising a ferrite of formula Fe2O3, MO, in which M represents Fe, Ba, Sr, Mn or Zn; and a step of applying, on the composition deposited in the previous step, a false eyelash comprising a magnetic base, to which a fringe of eyelashes is attached, said base comprising at least one magnet.

The composition containing magnetic particles can be in the form of an eyeliner or an eyeshadow.

The invention involves applying the composition containing magnetic particles, at least on the root of the eyelashes, in order to subsequently attach a magnetic false eyelash thereto, which eyelash remains in place due to the force of attraction with the magnetic particles.

According to a first variant, the length of the false eyelash can be substantially equal to the length of the eyes of the person, and can be applied on the eyelid over the entire length of the root of the eyelashes. In this case, the composition can be an eyeliner deposited in the form of a line at the root of the eyelashes, or an eye shadow deposited along the root of the eyelashes and on at least one other part of the eyelid. In this variant, only one magnetic false eyelash is applied on the eye.

According to a second variant, the length of the false eyelash is less than the length of the eyelid. In this case, one or more portions of false eyelashes can be fixed on the eyelid at the root of the eyelashes, but the false eyelash portions are all positioned on the same side of the natural eyelash fringe.

Magnetic Particles

The size of the preferred magnetic particles is less than 150 microns, preferably less than 100 microns, and more preferably less than 60 microns.

The term "size", within the meaning of the invention, is understood to be the average particle size, D50, D90, D95, D100 or any other definition known to a person skilled in the art. The size also can be the largest dimension of one of the magnetic particles contained in the magnetic composition.

The size of the particles can be measured using any microscopy method known to a person skilled in the art, such as laser microscopy.

In one embodiment, the magnetic particles can be characterized by a D50 value of between 0.05 and 0.3 microns, and/or by a D90 value of less than 5 microns.

The magnetic particles comprise a ferrite of formula Fe2O3, MO, in which M represents Fe, Ba, Sr, Mn or Zn. They can comprise, in addition to the ferrite, at least one other mineral compound that is selected, for example, from mica, aluminum hydroxide, titanium oxide and silicon oxide.

The magnetic particles preferably comprise more than 90% by mass of ferrite, which ferrite can be coated with a mineral coating, for example, a mineral coating comprising one of the compounds described above. Alternatively, the magnetic particles can comprise a mineral support coated with ferrite, for example, a mineral support comprising one of the compounds described above.

In a particular embodiment, M represents Fe and the ferrite is an iron oxide of formula Fe3O4. In this embodiment, the magnetic particles can have the INCI designation CI 77499 or IRON OXIDES.

The magnetic particles can be selected from:
particles comprising Fe3O4 coated with silica;
particles comprising Fe3O4 in octagonal form, the D50 value of which ranges from 1 to 2 microns;
particles comprising Fe3O4 and traces of other mineral oxides, the particles having a D50 value of the order of 0.10 to 0.20 microns;
magnetite particles having, for example, a D80 value of less than 100 microns; and
particles comprising a mica support and a coating of Fe3O4, with the particles being between 10 and 60 microns.

The magnetic particles may or may not be colored.

The magnetic composition can comprise from 20% to 99% by mass of magnetic particles comprising more than 95% by mass of a ferrite of formula Fe2O3, MO, in which M represents Fe, Ba, Sr, Mn or Zn.

The composition can comprise, for example, a quantity of magnetic particles that is greater than a value selected from 20%, 25%, 30%, 35%, 40%, 45%, 50%, 55%, 60%, 65%, 70%, 75%, 80%, 85%, 90%, and is less than a value selected from 99%, 95%, 90%, 85%, 80%, 75%, 70%, 65%, 60%, 55%, 50%, 45%, 40%, 35%, 30% and 25%, with the percentages being expressed by mass relative to the mass of the composition.

Galenics

The composition can have different galenic forms. It can be, for example, in the form of an aqueous dispersion, an anhydrous dispersion, a water-in-oil emulsion or an oil-in-water emulsion. Thus, the magnetic particles can be dispersed in a liquid or solid fatty phase, or in an aqueous phase. The magnetic composition can have any consistency, for example, fluid, pasty or solid.

According to a first embodiment, the composition is liquid in the form of a dispersion of magnetic particles in water.

According to a second embodiment, the composition is an anhydrous solid composition containing waxes obtained by hot casting a rod, for example.

According to a third embodiment, the composition is a powdery anhydrous solid composition comprising fillers that have been compacted with a fatty binder in the presence of the magnetic particles.

Preferably, the composition is not an anhydrous composition comprising too much oil, which may reduce the attraction force between the magnetic composition and the magnetic false eyelashes.

The magnetic composition can appear to the user to be colored or colorless in its packaging before application. A deposit of the magnetic composition on the eyelid can appear to be colored or colorless.

When the composition is fluid, its viscosity measured at an ambient temperature of 20° C. or 25° C. can be between 3,000 and 12,000 cPs. This viscosity can be measured with a Rhéolab QC viscometer (Anton Paar) equipped with Rheoplus software using a suitable spindle and measuring time (for example, 4-vane spindle ST22-4V, at 100 rpm, for 3 min). Prior to measurement, the composition of the invention will have been placed in a 120 ml jar.

The correct selection of the spindle is verified by measuring the percentage of deviation of the measurements that are taken every 6 seconds. The value of the viscosity of the composition is equal, according to this protocol, to the average of the last fifteen measurements taken by the apparatus during the measurement time indicated above.

According to one variant, the magnetic composition can be fluid, in the form of a dispersion of the magnetic particles in water. A particular fluid composition is an aqueous dispersion containing less than 5% by mass of oil. The major component of the aqueous dispersion is preferably water. The composition can comprise from 25% to 80% water and optionally an agent for dispersing said magnetic particles in a sufficient quantity for ensuring the homogeneity and stability of the composition. It can also comprise from 3% to 15% by mass of a polyol selected from glycerin, butylene glycol, pentylene glycol and mixtures thereof. Finally, the composition can further comprise at least one polymer, which is soluble or is dispersed in water, for example, a polyvinyl alcohol, a polyurethane, a polyacrylate or a mixture thereof. In a particular embodiment, the composition is a black liquid eyeliner containing from 0.2% to 0.6% by mass of a gelling polymer, from 5% to 20% by mass of a film-forming polymer, from 20% to 55% by mass of magnetic particles, from 3% to 15% by mass of at least one polyol, and from 25% to 70% by mass of water. The gelling polymer can have film-forming properties and the film-forming polymer can have gelling properties.

According to another variant, the magnetic composition is a molded, cast or pressed anhydrous composition comprising, in addition to the magnetic particles, powder compounds such as fillers or pigments. In this case, the composition can contain at least one binding fatty compound, which provides the mixture of magnetic particles and powders with cohesion. The binding fatty compound can be oily, pasty or waxy in consistency. A person skilled in the art will know how to select the type and to adapt the quantity of the fatty compound according to the desired texture.

The pigments can be selected from manganese violet, ultramarine blue, hydrated chromium oxide, ferric blue, carbon black, lacquers (made up of a water-soluble dye grafted onto a titanium dioxide support), and nacres (comprising a mica and/or titanium oxide support).

The fillers can be particularly selected from talc, micas, kaolin, metal soaps derived from organic carboxylic acids containing from 8 to 22 carbon atoms, zinc oxides, titanium oxides, calcium carbonate, magnesium carbonate, magnesium hydrocarbonate, silica, glass beads, ceramic beads, crosslinked or non-crosslinked starches, synthetic polymer powders, which may or may not be crosslinked, spheronized or expanded, such as powders of polyethylene, polyester, polyamide, poly(meth)acylate, polyurethane, divinylbenzene crosslinked polystyrene, silicone resin, such as silsesquioxanes, or tetrafluoroethylene.

A magnetic composition of the invention is in the form of a pressed powder comprising magnetic particles, fillers and pigments. The sum of the magnetic particle content, of the filler content and of the pigment content preferably represents from 50% to 99% by mass, for example, from 70% to 90% by mass, of the mass of the composition. The pressed powder can also contain from 5% to 30% by mass of a binding fatty compound.

The composition containing magnetic particles can be sold as eyeliner or eye shadow. It can be offered in the form of a pencil, in a bottle, or in a cup. Its function is to attach the magnetic false eyelash, and optionally to color the eyelids.

The magnetic composition can be applied as an eyeliner, by drawing a fairly thick, continuous or discontinuous line on the root of the eyelashes. The eyeliner composition can be applied with a brush, with a pad, or with a felt tip attached to the package containing the composition. The magnetic composition can be applied as an eyeshadow, on at least a part of the eyelid and on at least a part of the eyelash root.

Thus, the composition can be an eye shadow, an eyeliner or a kohl, and can be in the form of a stick, a cream, a powder, a gel or a more fluid liquid.

A liquid composition can be applied with a brush, a flocked applicator or a pad. It can be packaged in the reservoir of a felt pen or in a bottle.

A solid composition can be a powder applied with a sponge or a brush. It also can be in the form of a pencil lead integral with a stick or housed in a mechanical pencil with a retractable mechanism.

Magnetic Eyelashes

The false eyelash grips onto the deposited composition due to the attraction force between the magnetic base and the magnetic particles.

The magnetic base of the false eyelash comprises a single magnet or at least two magnets. The false eyelash therefore comprises one or more magnets, the number, size (particularly the length), and the arrangement of which on the base are adapted by a person skilled in the art depending on the shape of the false eyelash (degree of curvature, weight, length).

According to a first variant, the base of the false eyelash comprises a single magnet, the length of which is equal to the length of the base. When the false eyelash is short, it may comprise only one magnet that is shorter than the length of the base and is preferably located at the center thereof.

According to a second variant, the base comprises a plurality of magnets spaced apart at regular intervals on the base, so as to obtain satisfactory adhesion. The base can comprise two magnets located at each of the ends thereof.

According to a third variant, the base of the false eyelash is made up of a magnet, around which the eyelashes are wound.

The lashes of the false eyelashes can be natural material or synthetic material.

The base of the false eyelash can be selected or cut so that its length is equal to that of the eyelid of the person.

The base of the false eyelash also can be much smaller than the length of the eyelid and, in this case, it relates to a portion of a false eyelash. The portions of false eyelashes can be half-fringes or individual eyelashes. The composition therefore can be applied over the entire length of the root of the eyelashes or be applied over only part of the root of the eyelashes.

The false-eyelash portion can, for example, add a color effect to certain areas of the natural fringe or increase the density of the eyelashes of the person on a particular area. In this case, one or more portions of a false eyelash can be fixed on the same side of the fringe of natural eyelashes. The false eyelash can enhance the look, open the eyes, increase the density of the eyelashes, lengthen the eyelashes or color them.

In a particular embodiment of the invention, the magnetic base of the false eyelash comprises at least one magnet, the largest dimension of which is between 0.1 and 6 mm. When the magnetic base comprises a plurality of magnets, they can be identical or have different dimensions.

The magnet or the magnets (when there are several magnets) can be substantially parallelepipedal in shape and be between 0.1 and 0.5 mm thick, or be substantially cylindrical in shape, such as that of a wire, and have a diameter between 0.1 and 1 mm.

According to one embodiment, the magnet or the magnets is/are, independently of one another, between 0.1 and 2.0 mm thick, between 0.5 and 6.0 mm wide, and between 0.5 and 6.0 mm long. The magnets are preferably between 0.1 and 0.5 mm thick; preferably between 0.5 and 1.5 mm wide, and preferably between 1 and 4 mm long.

The magnet or the magnets can be made up of, independently of one another, a material selected from neodymium, steel, magnetite, ferrite, aluminum-nickel-cobalt alloy, sarium-cobalt alloy or hematite.

The magnet or the magnets emit, independently of one another, a magnetic field, the intensity of which is, for example, between 500 Gauss and 2,500 Gauss.

When the magnetic base comprises a plurality of magnets, it is preferred that the total magnetic force generated by the set of magnets is greater than or equal to 1,500 Gauss and less than or equal to 2,500 Gauss.

According to a particular embodiment, the base of the false eyelash comprises two magnets, each of the magnets being located at one of the ends of the base.

According to another embodiment, the base of the false eyelash comprises at least two, three, four, five or six magnets, two of which are located on the ends of the base. The length of the magnets positioned on the ends of the base ("external" magnets) is preferably greater than or equal to that of the other magnets ("internal" magnets). The set of external and internal magnets can be an odd number, with the external magnets being identical, and the internal magnets can alternately comprise a magnet having at least one dimension smaller than that of the external magnets, and a magnet having at least one dimension identical to that of the external magnets.

The external magnets preferably are between 0.3 and 0.5 mm thick, between 0.5 and 1.5 mm wide and between 2 and 4 mm long, while the internal magnets, when present, are preferably thinner than the external magnets, preferably between 0.1 and 0.3 mm. The length of the internal magnets can be equal to or less than that of the external magnets. The internal magnets do not necessarily all have the same dimensions. A person skilled in the art will be able to adjust the dimensions, the number and the arrangement of the magnets on the base in order to modulate the adhesion properties of the false eyelash on the liner according to the composition of said liner.

According to another embodiment, the false eyelash comprises a single magnet, the length of which is equal to that of the base of the false eyelash.

The false eyelash can comprise a fringe of synthetic fibers or natural eyelashes that can be identical or different in terms of length, color and/or thickness. The false eyelash can provide different makeup results, depending on the nature of the fringe. For example, the material, shape, density, color, length and bending of the false-eyelash fibers or eyelashes can vary to create a natural, dense, long, curved, black, colored or mother-of-pearl effect. Some of the fibers can be feather-shaped or bear rhinestones.

The length of the fringe can vary depending on the desired effect. The false eyelash can be customized to fit the length and shape of the eyes of the person.

In one embodiment, the method of the invention can comprise, prior to the two application steps, a step of selecting, by the user, the false eyelash from a set comprising a plurality of false eyelashes, and a step of selecting, by the user, the magnetic composition from a set of a plurality of different magnetic compositions, with the selections being informed by the shape of the eyes of the user and by the makeup effect sought by the user, with said magnetic compositions of the set of compositions being independent of one another in accordance with one of the magnetic compositions described above, and said false eyelashes of the set of false eyelashes being independent of one another in accordance with one of the false eyelashes described previously.

In the context of this embodiment, the set of false eyelashes can be offered for sale in the same package, the set of compositions also can be offered for sale in the same package. In another variant, a product comprising at least two false eyelashes and at least one composition can be offered for sale in the same package. In this case, the product can comprise at least two compositions, including at least one eyeliner and at least one eyeshadow.

To better inform their selection, the user can, at the point of sale or at home, perform a digital simulation of the aesthetic result obtained with a given pair of false eyelashes and a given composition. This simulation can be obtained from a bank of images or drawings. The user can also use an augmented reality application and simulate the result from one of their photographs.

The invention therefore also relates to an eye makeup product comprising at least one magnetic composition comprising a homogeneous dispersion of magnetic particles of formula $Fe_2O_3$, MO, in which M represents Fe, Ba, Sr, Mn or Zn, and at least two false eyelashes comprising a magnetic base, to which a fringe of eyelashes is attached, said base comprising at least one magnet.

The features relating to the magnetic composition and to the false-eyelash that have been described above in connection with the makeup method of the invention apply to the makeup product of the invention.

The invention also relates to an eyelid makeup composition containing from 20% to 99% by mass of magnetic particles comprising more than 95% by mass of a ferrite of formula $Fe_2O_3$, MO, in which M represents Fe, Ba, Sr, Mn or Zn.

The features that have been described to characterize the makeup method of the invention can be applied to the composition of the invention as appropriate.

Finally, the invention relates to the use of a composition containing from 20% to 99% by mass, preferably from 25% to 35% by mass, of magnetic particles, said magnetic particles comprising more than 95% by mass of a ferrite of formula $Fe_2O_3$, MO, in which M represents Fe, Ba, Sr, Mn or Zn, as a means for fixing false eyelashes on eyelids.

The invention also relates to an eye makeup method implementing a method for applying false eyelashes as described above. The eye makeup method can comprise the use of at least one magnetic composition described above, but also the use of additional makeup products. The false eyelash application method of the invention itself can be an eye makeup method when, in particular, the magnetic composition alone provides a visual effect that changes the appearance of the eyes.

The invention is further illustrated by the following embodiments.

Examples 1 to 7

Black eye liners were prepared. Their composition is provided in Table 1 below. The percentages are by mass.

TABLE 1

| Chemical name or INCI | Trade name | Ex. 1 | Ex. 2 | Ex. 3 | Ex. 4 | Ex. 5 | Ex. 6 | Ex. 7 |
|---|---|---|---|---|---|---|---|---|
| Xanthan gum | Rhodicare XC | 0.5 | 0.5 | 0.5 | 0.3 | 0.3 | 0.5 | 0.5 |
| Polyvinyl alcohol | Selvol Ultalux FP | 10 | 10 | 10 | 8 | 7 | 10 | 10 |

TABLE 1-continued

| Chemical name or INCI | Trade name | Ex. 1 | Ex. 2 | Ex. 3 | Ex. 4 | Ex. 5 | Ex. 6 | Ex. 7 |
|---|---|---|---|---|---|---|---|---|
| Acrylate copolymer | Covacryl A15WP | 22 | 22 | 22 | 15 | 10 | 22 | 22 |
| Iron oxide | C337001 Sunpuro Black Iron oxide | 30 | | | | | | |
| Iron oxide and silica | Sympholigth BW | | 30 | | 40 | 50 | | |
| Iron oxide | Tarox Iron Oxide | | | 30 | | | | |
| Sand | Microzest 50 Magnetite | | | | | | 30 | |
| Iron oxides, mica and titanium dioxide | Colorona Mica black | | | | | | | 30 |
| Glycerin | | 4.5 | 4.5 | 4.5 | 2 | 1.5 | 4.5 | 4.5 |
| Butylene glycol | | 4.5 | 4.5 | 4.5 | 2 | 1.5 | 4.5 | 4.5 |
| Pentylene glycol | | 3 | 3 | 3 | 3 | 3 | 3 | 3 |
| Phenoxyethanol | | 0.25 | 0.25 | 0.25 | 0.25 | 0.25 | 0.25 | 0.25 |
| Water | | Qs 100 | Qs 100 | Qs 100 | Qs 100 | Qs 100 | Qs 100 | Qs 100 |

The compositions were all stable and homogeneous at 20° C. for 24 hours. The value of their viscosity is listed in Table 2 below, with the method of measuring the viscosity being the same as that described above in the description.

Volunteers successively evaluated each of these eyeliners by applying them with a brush on the root of the upper lashes of their eyes. They allowed it to dry, and then applied a Magnetic Eyelashes CLICK LASH—Natural Look® false eyelash, which is sold by SPITZER & HELMLE UG, on the eyeliner deposit.

The result of these evaluations is listed in Table 2.

TABLE 2

| Properties | Ex. 1 | Ex. 2 | Ex. 3 | Ex. 4 | Ex. 5 | Ex. 6 | Ex. 7 |
|---|---|---|---|---|---|---|---|
| Viscosity in cPs at 25° C. (spindle ST 22 - 4 V) | 11375 | 3437 | 6712 | 3461 | 4870 | 3128 | 3489 |
| Thickness of the dry film | +++ | + | +++ | ++ | +++ | + | ++ |
| Adhesion of false eyelashes on the eyelids | +++ | ++ | +++ | ++ | +++ | ++++ | + |

Thickness of the Film:

| + | thin |
| ++ | moderately thick |
| +++ | thick |

Adhesion of False Eyelashes on the Eyelids:

| + | poor |
| ++ | average |
| +++ | strong |

Examples 8 to 10

The inventors conducted a second study comparable to that of the study of Examples 1 to 7, by preparing three compositions of liquid eyeliners and by evaluating the behavior of magnetic false eyelashes with these compositions. The magnetic false eyelashes used are identical to those used in Examples 1 to 7, namely Magnetic Eyelashes CLIC LASH—Natural Look® (force 1620 Gauss) sold by SPITZER & HELMLE UG. The method for measuring the viscosity is the same as that described above in the description.

The compositions of the eyeliners and the results that were obtained are shown in Table 3. The percentages are by mass.

TABLE 3

| Chemical name or INCI | Trade name | Ex. 8 | Ex. 9 | Ex. 10 |
|---|---|---|---|---|
| Xanthan gum | Rhodicare XC | 0.3 | 0.5 | 0.5 |
| Polyvinyl alcohol | Selvol Ultalux FP | — | 5 | 3 |
| Acrylate copolymer | Syntran PE 5760 302-7 | — | — | 29 |
| Polyurethane-35 | Baycusan C1004 | 17 | 27 | — |
| Iron oxide | C33-7001 Sunpuro Black Iron oxide | — | — | 30 |
| Iron oxide and silica | Sympholigth BW | 50 | — | — |
| Iron oxide | Tarox Iron Oxide | — | 30 | — |
| Glycerin | | 1.5 | 4.5 | 9 |
| Butylene glycol | | 1.5 | 4.5 | — |
| Pentylene glycol | | 3 | 3 | 3 |
| Phenoxyethanol | | 0.25 | 0.25 | 0.25 |
| Water | | Qs 100 | Qs 100 | Qs 100 |
| Viscosity in cPs at 25° C. (spindle ST 22 - 4 V) | | 1299 | 5731 | 2428 |
| Liner application | | easy | easy | easy |
| Thickness of deposited film | | ++ | + | + |
| Adhesion of false eyelashes on the eyelids at T 0 h | | +++ | +++ | +++ |
| Repositioning false eyelashes | | easy | easy | easy |
| Make-up removal (with make-up remover lotion) | | Easy | Very easy | easy |

The invention claimed is:

1. A method for applying false eyelashes on a person, comprising:
   a step of applying, on the eyelid, a magnetic composition comprising a homogenous dispersion of 20% to 55% by mass of magnetic particles, said magnetic particles comprising more than 90% by mass of a ferrite of formula $Fe_2O_3$, MO, in which M represents Fe, Ba, Sr, Mn or Zn; and
   a step of applying, on the composition deposited in the previous step, a false eyelash comprising a magnetic base, to which a fringe of eyelashes is attached, said base comprising at least one magnet.

2. The method according to claim 1, characterized in that the size of the magnetic particles is less than 150 microns.

3. The method according to claim 1, characterized in that the magnetic particles comprise, in addition to the ferrite, at least one other compound selected from mica, aluminum hydroxide, titanium oxide and silicon oxide.

4. The method according claim 1, characterized in that the composition contains from 30% to 45% by mass of magnetic particles.

5. The method according to claim 1, characterized in that the composition is liquid in the form of a dispersion of magnetic particles in water.

6. The method according to claim 5, characterized in that the composition comprises from 25% to 80% of water and a dispersing agent.

7. The method according to claim 5, characterized in that the composition contains from 3% to 15% by mass of a polyol selected from glycerin, butylene glycol, pentylene glycol and mixtures thereof.

8. The method according to claim 5, characterized in that the composition further comprises at least one polymer chosen from polyvinyl alcohols, polyurethanes, polyacrylates, or mixtures thereof.

9. The method according to claim 1, characterized in that the composition is a molded, cast or pressed anhydrous composition comprising, in addition to the magnetic particles, powder compounds and at least one binding fatty compound.

10. The method according to claim 1, characterized in that the magnet is between 0.1 and 2.0 mm thick, between 0.5 and 6.0 mm wide and between 0.5 and 6.0 mm long.

11. The method according to claim 1, characterized in that the composition is an eye-liner or eyeshadow offered in the form of a pencil, in a bottle or in a cup.

12. A product for eye makeup comprising at least one magnetic composition comprising a homogeneous dispersion of 20% to 50% by mass of magnetic particles comprising at least 90% by mass of formula $Fe_2O_3$, MO, in which M represents Fe, Ba, Sr, Mn or Zn, and at least two false eyelashes comprising a magnetic base, to which a fringe of eyelashes is attached, said base comprising at least one magnet.

13. The method according to claim 1, wherein the ferrite is $Fe_3O_4$.

14. The method according to claim 1, wherein the magnetic particles comprise at least 95% by mass of formula $Fe_2O_3$, MO.

15. The method according to claim 8, wherein the at least one polymer is present in an amount ranging from 5% to 20% by mass.

16. The method according to claim 8, wherein the at least one polymer is an acrylate copolymer.

17. The method according to claim 8, wherein the at least one polymer is a polyurethane.

18. The method according to claim 1, characterized in that the size of the magnetic particles is less than 100 microns.

* * * * *